US008636951B2

(12) United States Patent
Shannon et al.

(10) Patent No.: US 8,636,951 B2
(45) Date of Patent: *Jan. 28, 2014

(54) BIO-TERRORISM COUNTERACTION USING OZONE AND HYDROGEN PEROXIDE

(75) Inventors: Michael Edward Shannon, Picton (CA); Dick Eric Zoutman, Kingston (CA)

(73) Assignee: Medizone International, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 13/522,685

(22) PCT Filed: Sep. 8, 2010

(86) PCT No.: PCT/CA2010/001364
§ 371 (c)(1),
(2), (4) Date: Aug. 27, 2012

(87) PCT Pub. No.: WO2011/085466
PCT Pub. Date: Jul. 21, 2011

(65) Prior Publication Data
US 2012/0315188 A1      Dec. 13, 2012

Related U.S. Application Data

(63) Continuation of application No. PCT/CA2010/000998, filed on Jul. 5, 2010.

(60) Provisional application No. 61/295,851, filed on Jan. 18, 2010.

(51) Int. Cl.
*A61L 2/20* (2006.01)
(52) U.S. Cl.
USPC ................................................. 422/28

(58) Field of Classification Search
USPC ..................................... 422/4, 28, 30
See application file for complete search history.

(56) References Cited

U.S. PATENT DOCUMENTS

| 5,316,741 | A | * | 5/1994 | Sewell et al. ............ 422/186.21 |
| 6,045,846 | A | | 4/2000 | Bautista et al. |
| 7,217,685 | B2 | | 5/2007 | McDonnell et al. |
| 7,393,818 | B2 | | 7/2008 | McDonnell et al. |

(Continued)

FOREIGN PATENT DOCUMENTS

| CA | 2486831 A1 | 2/2004 |
| CA | 2547589 A1 | 7/2005 |

(Continued)

OTHER PUBLICATIONS

Prospects for Managed Underground Storage of Recoverable Water, National Research Council. 2008. p. 243.*

(Continued)

*Primary Examiner* — Sean E Conley
*Assistant Examiner* — Donald Spamer
(74) *Attorney, Agent, or Firm* — Durham Jones & Pinegar Intellectual Property Law Group

(57) ABSTRACT

A process and a system using a disinfecting atmosphere for deactivating *Bacillus* bacteria and its spores, such as *Bacillus anthracis* (anthrax) and *C Botulinum* and its spores, commonly proposed as bioterrorism threats, are described. Said disinfecting atmosphere includes ozone at a concentration of 2-350 ppm by weight and hydrogen peroxide at an amount of 0.2-10 weight percent at a relative humidity of at least 60%.

19 Claims, 4 Drawing Sheets

(56) References Cited

U.S. PATENT DOCUMENTS

| | | | |
|---|---|---|---|
| 7,407,624 | B2 | 8/2008 | Cumberland et al. |
| 8,551,399 | B2 | 10/2013 | Shannon et al. |
| 2003/0039729 | A1* | 2/2003 | Murphy et al. ............... 426/320 |
| 2003/0132279 | A1* | 7/2003 | Stemmle .......................... 232/31 |
| 2005/0129571 | A1* | 6/2005 | Centanni .......................... 422/31 |
| 2005/0226764 | A1 | 10/2005 | Moirandat et al. |
| 2006/0104858 | A1 | 5/2006 | Potember et al. |
| 2007/0079455 | A1* | 4/2007 | Brewer et al. ................... 15/22.2 |
| 2008/0031770 | A1* | 2/2008 | Heselton et al. ................. 422/4 |
| 2009/0263499 | A1 | 10/2009 | Platt, Jr. et al. |

FOREIGN PATENT DOCUMENTS

| | | | |
|---|---|---|---|
| WO | 2004011041 | A2 | 2/2004 |
| WO | 2005060385 | A2 | 7/2005 |
| WO | 2009046562 | A2 | 4/2009 |
| WO | 2011003179 | A1 | 1/2011 |
| WO | 2011085466 | A1 | 7/2011 |

OTHER PUBLICATIONS

Whitney et al., "Inactivation of *Bacillus anthracis* Spores", Emerging Infectious Diseases, Jun. 2003, vol. 9, No. 6, pp. 623-627, available at http://wwwnc.cdc.gov/eid/article/9/6/pdfs/2-0377.pdf.

Rogers et al., "*Bacillus anthracis* Spore Inactivation by Fumigant Decontamination", Applied Biosafety, 2008, vol. 13, No. 2, pp. 89-98, available at http://www.absa.org/abj/abj/081302Rogers.pdf.

PCT International Search Report and Written Opinion, PCT/CA2010/001364, dated Dec. 3, 2010.

Canadian Intellectual Property Office, "International Search Report and Written Opinion," issued in International Patent Application No. PCT/CA2011/050544, dated Dec. 28, 2011.

Canadian Intellectual Property Office, "International Search Report and Written Opinion," issued in International Patent Application No. PCT/CA2011/050543, dated Dec. 19, 2011.

Canadian Intellectual Property Office, "International Search Report and Written Opinion," issued in International Patent Application No. PCT/CA2011/050542, dated Dec. 9, 2011.

United States Patent and Trademark Office, "Office Action," issued in U.S. Appl. No. 13/343,403, dated Oct. 25, 2012.

Canadian Intellectual Property Office, "International Search Report and Written Opinion," issued in International Patent Application No. PCT/CA2010/000998, dated Oct. 7, 2010.

Canadian Intellectual Property Office, "International Search Report and Written Opinion," issued in International Patent Application No. PCT/CA2010/000998, dated Jul. 27, 2011.

Dr. Carsten Matz, et al., "Biofilm Bacteria Protect Themselves with Chemical Weapons", Helmholtz Centre for Infection Research, Bauschweig, reported on Inforniac.com, Jul. 23, 2008.

"Ozone effects on specific bacteria, molds and viruses—ozone and bacteria destruction" published Dec. 24, 2007, http://web.archive.org/web20071224191320/http://www.ozoneapplications.com/info/ozone_bacteria_mold_viruses.htm.

Richard P. Wenzel, et al., "The Impact of Hospital-Acquired Bloodstream Infections", Emerging Infectious Diseases, vol. 7, No. 2, Mar.-Apr. 2001, pp. 174-177.

United States Patent and Trademark Office, "Office Action," issued in U.S. Appl. No. 13/343,403, dated Mar. 25, 2013.

"Amendment after Non-Final Rejection and Notice of Non-Compliant Amendment," filed Feb. 25, 2013 in U.S. Appl. No. 13/343,403 in response to Notice of Non-Complaint Amendment of Feb. 20, 2013, and Non-Final Office Action of Oct. 25, 2012.

"Amendment Under 37 C.F.R. §1.116 With Request for Consideration Under the Final Consideration Pilot Program 2.0," filed Jun. 25, 2013 in U.S. Appl. No. 13/343,403 in response to final Office Action of Mar. 25, 2013.

"Supplemental Amendment," filed Jul. 19, 2013 in U.S. Appl. No. 13/343,403 in response to final Office Action of Mar. 25, 2013 and the telephonic interview with the Examiner of Jul. 19, 2013.

United States Patent and Trademark Office, "Notice of Allowability," issued in U.S. Appl. No. 13/343,403, dated Aug. 2, 2013.

"Comments on Statement of Reasons for Allowance," filed Sep. 6, 2013 in U.S. Appl. No. 13/343,403 in response to Notice of Allowability of Aug. 2, 2013.

* cited by examiner

BIO-TERRORISM COUNTERACTION USING OZONE AND HYDROGEN PEROXIDE

CROSS-REFERENCE TO RELATED APPLICATIONS

This application is the national stage under 35 U.S.C. §371 of International Patent Application No. PCT/CA2010/001364 filed Sep. 8, 2010, designating the United States, and published Jul. 21, 2011 as International Publication No. WO/2011/0855466, which application claims priority to and the benefit of International Patent Application PCT/CA2010/000998 filed Jul. 5, 2010 and published Jul. 13, 2011 as International Publication No. WO/2011/003179, which application claims priority to and the benefit of U.S. Patent Application Ser. No. 61/295,851 filed on Jan. 18, 2010. The disclosures of the above-identified applications are expressly incorporated herein by this reference in their entireties.

FIELD OF THE INVENTION

This invention relates to bacterial infection and methods and systems for counteracting and avoiding deliberate attempts to cause bacterial infections in humans and other mammals. More particularly, it relates to methods and systems for inactivating spores of the bacterium *Bacillus anthracis* and *Claustridium botulinum*, the primary bacteria associated with a bio-terrorism attack.

BACKGROUND OF THE INVENTION

Of growing concern are threatened bioterrorist and warfare attacks using potentially lethal bacteria highly resistant to extreme environmental conditions. Some of the deadliest bacteria, for example anthrax (*Bacillus anthracis*), are also highly resistant to conventional sterilization agents and protocols. Contamination of public facilities with such bacteria constitutes a significant threat to human life with residual amounts of such bacteria being almost impossible to remove using current methods. Accordingly, building remediation has become a major priority among G8 nations (Dr. Steven Jones, Chair of the WHO Emerging and Dangerous Pathogens Committee, June, 2010).

*Bacillus anthracis* bacteria spores have a very long lifetime. At animal burial sites, they have been known to re-infect animals over 70 years after burial of an anthrax-killed animal.

There are many (c. 90) known strains of anthrax. The Vollum strain was developed but never used as a biological weapon during World War II, and is a particularly virulent strain. Another virulent strain is the Ames strain, which was used in 2001 anthrax bioterrorism attacks in the United States.

Anthrax can enter the human body by ingestion through the intestines, by inhalation through the lungs, or cutaneously through the skin. All three infection routes are of concern in the context of bioterrorism attacks with bacteria such as anthrax, but inhalation of an anthrax-contaminated environment in an enclosed room, and skin contact with anthrax contaminated objects, are of special concern since either or both can result from receipt of anthrax contaminated objects into an enclosed space such as an office. Respiratory infection with anthrax in humans initially manifests itself as cold or flu-like symptoms for several days, but then progresses quite suddenly to severe and commonly fatal respiratory collapse. If diagnosed early, anthrax infections can be treated with appropriate antibiotics, but not after the disease has progressed. Anti-anthrax vaccine is available for those known to be likely candidates for exposure, but this is not practical as a defense against anthrax-based bioterrorism.

Because of the dangers of experimenting with the highly toxic anthrax bacterium and its spores, it is common to experiment with another, less dangerous *Bacillus* species as a surrogate for anthrax, for example *Bacillus subtilis*. Results of deactivation treatment of *B. subtilis* are generally accepted as reliable indicators of effectiveness against *Bacillus anthracis*.

BRIEF REFERENCE TO THE PRIOR ART

Anthrax spores can survive for long periods of time in the environment after release. Oxidizing agents (chlorine dioxide, peroxides, ethylene oxide, sodium hypochlorite and the like) are commonly used to clean anthrax-contaminated sites, but these are relatively slow-acting. Such clean-up is time-consuming and costly, since the room facility must remain out of commission for extended periods of time. Soft and porous fabric surfaces pose a particular problem, since they will harbor live anthrax spores and render them inaccessible to routine liquid or gaseous treatments.

Vaporized hydrogen peroxide (VHP) is highly effective when applied to smooth surfaces, but has little or no efficacy on porous materials and fabrics. Moreover, VHP is very damaging to electronic devices.

Once a porous, soft surface such as carpet, drapery, bedding, porous material in ceilings and the like becomes impregnated with anthrax spores, it cannot be effectively disinfected using currently available agents and processes.

Ozone is known to be a powerful anti-bacterial, anti-fungal and anti-viral agent. For over 100 years, it has been used for water purification. It is known to be effective against *Legionella* Bacteria, *E. coli* and pseudomonas populations in such plants.

U.S. Pat. No. 7,407,624 (Cumberland et al.), issued Aug. 5, 2008, describes methods for abating allergens, pathogens, odours and volatile organic compounds in air, using an atmosphere having specific combinations of ozone concentration, hydrogen peroxide concentrations, temperature and humidity delivered over a period of time. The patent contains an experimental account of treating rooms of a residence, effectively treating cladosporium mold spores and penicillium/aspergillus molds in the room air. No details of the precise conditions are given. There is no demonstration or disclosure of treatment of contaminated surfaces in a room. The general disclosure of the patent states that selected conditions of ozone concentration, hydrogen peroxide, humidity and temperature are effective in killing anthrax pathogen, at ozone concentrations below 6-9 ppm, but the precise conditions used are not disclosed. In general, the patent teaches used in an atmosphere of 2-10 ppm ozone, hydrogen peroxide which is 75%-150% by weight of the atmospheric ozone concentration, at a temperature of 15-27° C. and time 0.5-3 hours. Many other airborne pathogens, including, anthrax, are said to be treatable by this method, but no experimental evidence is offered.

It is an object of the present invention to provide a novel and effective method of treating anthrax spore-infected objects and facilities.

SUMMARY OF THE INVENTION

The present invention provides, from one aspect, a process of combating both anthrax and *C. botulinum* bacteria and spores thereof in an enclosed space, which comprises exposing both the bacterium and its spores in the space to a disinfecting atmosphere which includes ozone at a concentration of 2-350 ppm by weight and hydrogen peroxide at an amount of 0.2-10 wt. %, at a relative humidity of at least 60%, and for a period of at least 30 minutes sufficient for an effective kill of the bacterium and spores; and subsequently removing ozone from the atmosphere, down to 0.04 ppm or less.

Another aspect of the invention provides a portable system for destroying *Bacillus* and *Claustridium* bacteria and spores thereof, including *Bacillus anthracis, Bacillus subtilis* and *Claustridium botulinum*, in rooms and on surfaces and equipment therein, comprising an ozone generator for discharging into the room a gaseous mixture including ozone; an ozone controller adapted to control the amount of discharged ozone; a source of hydrogen peroxide for discharging controlled amounts of hydrogen peroxide into the room; means for discharging the hydrogen peroxide and ozone into the room; humidity adjusting means adapted to increase or decrease the relative humidity of the room during treatment; and an ozone remover adapted to destroy ozone, down to a safe level in the room atmosphere for subsequent human utilization.

BRIEF REFERENCE TO THE DRAWINGS

FIG. 1 of the accompanying drawings is a diagrammatic illustration of an apparatus in accordance with an embodiment of the invention, disposed within a room to be disinfected.

THE PREFERRED EMBODIMENTS

Figure 1:
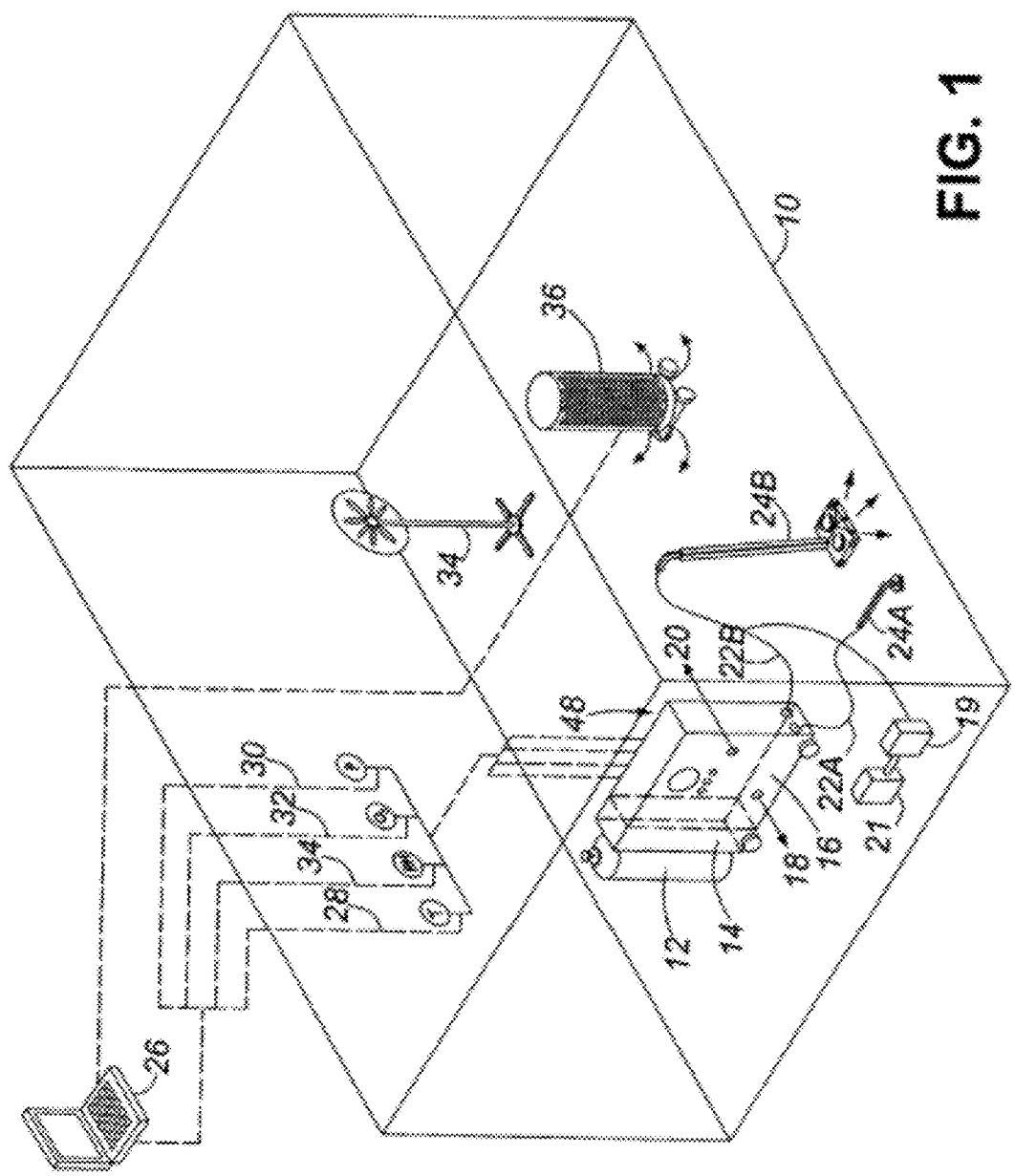
Figure 2A:
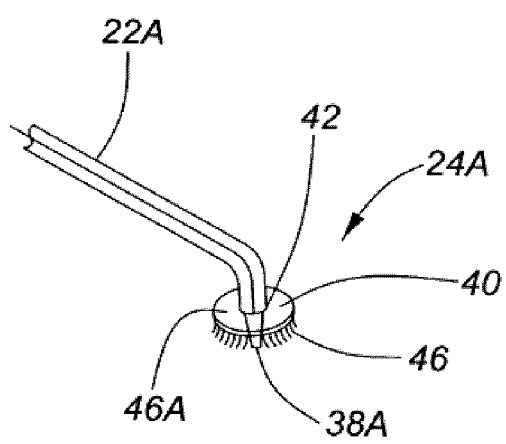
FIGS. 2A and 2B are diagrammatic illustrations of physical agitation systems for use in embodiments of the invention.
Figure 2B:
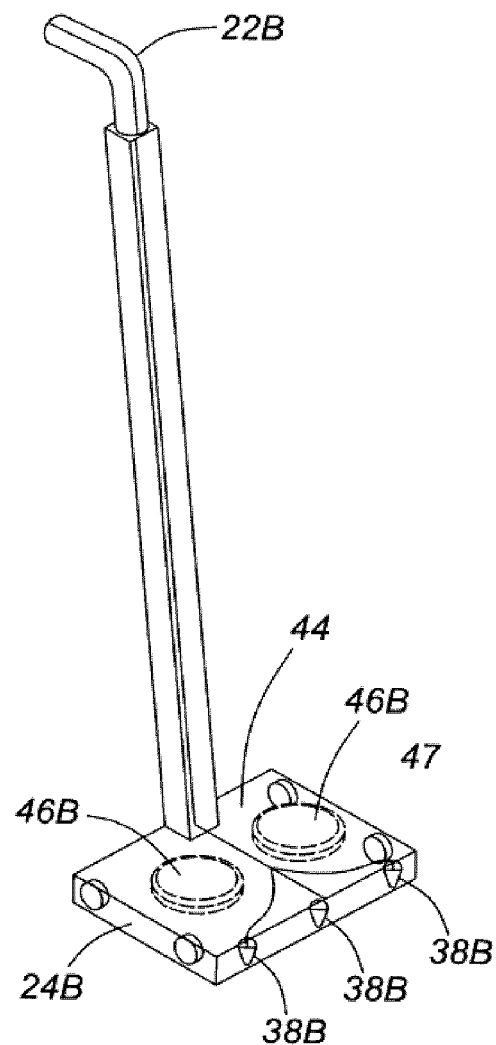
Figure 3:
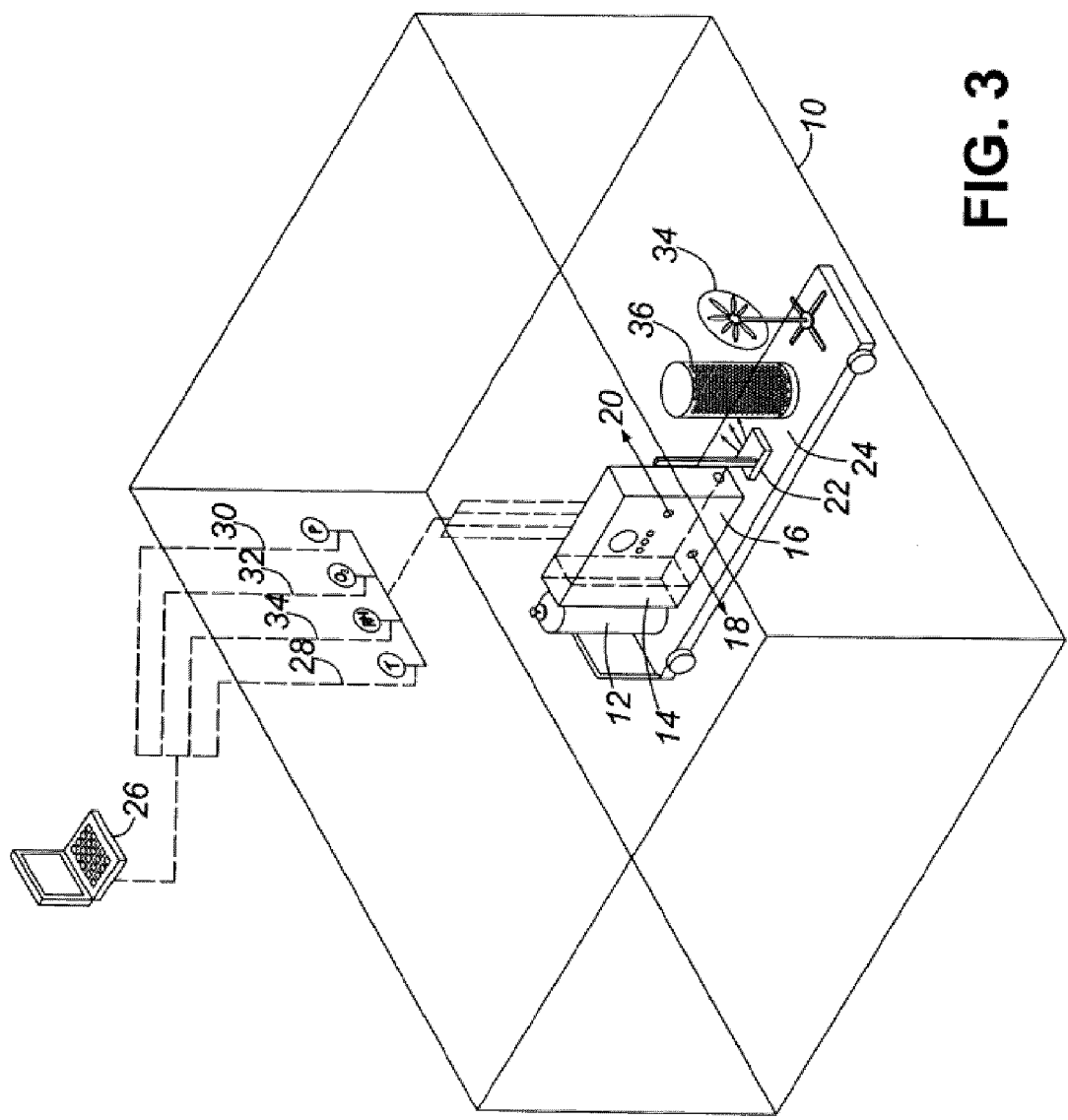
FIG. 3 is a diagrammatic illustration of an apparatus according to the invention, in portable, transportation mode.

Preferred ozone amounts for use in the invention are from about 20-350 parts per million in the disinfection atmosphere, more preferably 20-200, even more preferably 20-90 parts per million in the oxygen/ozone gas mixture, and most preferably 35-80 ppm ozone. Preferred amounts of hydrogen peroxide are the amounts supplied to the disinfecting atmosphere using an aqueous solution containing 0.2-10%, more preferably 1-5%, hydrogen peroxide. In the description below, the peroxide percentages used are sometimes expressed in terms of these solution percentages. The amounts are chosen so that no serious deleterious effects are suffered by other equipment in the treatment room to which the disinfecting atmosphere is supplied. The amount of hydrogen peroxide in the disinfecting atmosphere can be calculated from the volume of aqueous hydrogen peroxide evaporated into the disinfecting atmosphere, the volume of the room being disinfected and the concentration of hydrogen peroxide in the starting solution. Times of exposure of the room and its surface to the disinfecting atmosphere are suitably from 30 minutes to about 120 minutes, preferably from about 60 to about 105 minutes, and most preferably about 90 minutes. These times are constrained to some extent by the need to clear the room of ozone (down to a maximum of 0.04 ppm) following the disinfection phase, and return the room to normal use within a reasonable period of time, with the entire start-to-finish time not exceeding 150 minutes. The ozone removal is an extremely rapid and fully effective process. Both the hydrogen peroxide and the ozone (and any products of interaction between them) should be removed before the room is put back into normal use.

The preferred portable system for destroying *Bacillus* according to the present invention includes, as part of its means for discharging the hydrogen peroxide and ozone into the room, a dislodgement system at the outlet end of the discharging means. The dislodgement system allows penetration of carpet, drape and similar surfaces in the room, to gain access to concealed/sequestered spores and/or colonies of *Bacillus* bacteria, and to attack *Bacillus* bacteria and spores protected by a biofilm formed on surfaces in the room and embedding the bacteria and spores therein. The dislodgement system can be manually operated, with operators protected by a hazard suit and mask, or remotely operated or totally automated. It may take the form of one or more outlet jets, with associated manually operable jet pressure controls. It may take the form of a revolving or fixed brush with bristles of appropriate stiffness, alone or in combination with an outlet jet. Any form of dislodgement system effective to disturb the pile of carpet fabrics, upholstery fabrics and the like so as to access the remote parts which might harbor anthrax spores or colonies can be used. This includes non-physical applications such as air jets, ultrasonic energy radio-frequency energy and electromagnetic waves, for example, capable of causing physical disruption and which result in micro-physical movements of fibrous surfaces.

The ozone for use in the present invention can be generated by any known means. In the case of corona or other electrical discharge generation from oxygen, the apparatus of the invention preferably includes a container of medical grade oxygen. The oxygen container can be a standard, pressurized vessel containing medical grade oxygen, of the type commonly found in medical facilities. Oxygen from this container is fed to an ozone generator, where the oxygen is subjected to electrical discharge, normally with high voltage alternating current, to convert small amounts of the oxygen to ozone and produce a gaseous mixture of oxygen and ozone. The quantity of ozone in the mixture is controllable by adjustment of the voltage of the electrical discharge. Suitable ozone generators are known and available commercially. The relative amounts of ozone generated are relatively small, expressed in parts per million (ppm), but such is the power of ozone as a disinfectant, especially in combination with hydrogen peroxide in accordance with this invention, that such small quantities thereof are all that is required.

Alternative forms of ozone generation can be used if preferred. Ultraviolet radiation of appropriate wavelength, incident upon oxygen or air, is one acceptable alternative. In such a system, air from the room itself may be fed into the ozone generating unit to supply the required oxygen for conversion to ozone. Other methods of ozone generation which can be used include photocatalytic reactions, cold plasma, etc.

The relative humidity of the disinfecting atmosphere in the treatment space should be at least 60% and preferably at least 65%, for effective disinfection. To ensure this, one can incorporate a humidifier in the system of the invention, using sterile water from an internal system reservoir to adjust and control the humidity of the issuing gas mixture. In this way, desirable humidity for most effective disinfection is achieved at the point of discharge where dislodgement of a carpet or drapery surface can take place. Since the adjustable humidifier need only increase the humidity of the space to the desirable level, however, it can be placed in any location within the space. In one embodiment, the hydrogen peroxide vapor is applied, in controlled amounts, to the air/water vapor issuing from the humidifier and thus added to the ozone/oxygen containing gas mixture. Alternatively, hydrogen peroxide can be applied to the water used to humidify the target location. Hydrogen peroxide is commercially available as aqueous solutions of standard concentrations of hydrogen peroxide.

For use in embodiments of the present invention, a standard solution of known peroxide concentration is suitably diluted down by a fixed volume of distilled water. The peroxide load is standardized based on the known volume of water from the peroxide solution required to raise the relative humidity to the desired extent, e.g. from 40-80%. From this, the amount of hydrogen peroxide in volume % or ppm by volume introduced into the treatment facility can be calculated.

Certain systems according to embodiments of the invention may include a temperature adjuster and controller for the gas mixture. This can be a simple heater/cooler through which either the incident oxygen or the generated oxygen/ozone mixture passes prior to discharge into the room atmosphere. While simple adjustment of the temperature of the room using an external room heating system and thermostat can be effective, it is preferred to adjust the temperature of the issuing gas mixture, for most effective treatment of the carpet and drapery surfaces. The ideal range of temperature for ozone and ozone/hydrogen peroxide decontamination of *Bacillus* is 15° C. to 30° C.

The system of the invention also preferably includes an ozone removal unit. Such units are known, and can be purchased commercially for use in the present invention. Depending on the volume of the room atmosphere and the capacity of the ozone removal unit, more than one such unit may be incorporated in the system of the invention. Suitable ozone removal units are those based on activated carbon as the removal medium. These act very quickly, and do not lead to the formation of hazardous reaction products. The inclusion of such units enables the treated facility to be cleared of ozone and returned to normal use rapidly, for economic reasons. Other types include systems based on catalysts such as manganese oxide or other metal oxides, which may be heated to remove moisture, thermal destruction in conjunction with other metals including platinum or palladium.

FIG. 1 of the accompanying drawings shows a room 10 suspected of anthrax contamination and closed ready for disinfection by a process according to an embodiment of the invention. The room is substantially hermetically sealed. Inside the room is a pressurized cylinder 12 of oxygen, feeding oxygen gas into a humidifier 14 and thence to an ozone generator 16, which includes electrical discharge plates of variable voltage to adjust the quantity of ozone which is generated. A heater and a pressure controller (not shown) may be disposed near the entrance to the ozone generator. Output of oxygen/ozone gas mixture is via room outlets 18, 20 to the atmosphere of the room 10, and via wands 22A and/or 22B to a dislodgement means in the form of scrubbing brushes 24A and 24B mounted on the outlet ends of the respective wands 22A, 22B. The heater, the pressure controller, the voltage supplied to the ozone generator 16 and the humidity level supplied by the humidifier 14 are all controlled and adjusted from an external control panel 26 via respective electrical connections 28, 30, 32 and 34. Also disposed within the room is an oscillating fan 34 and an ozone destruct filter unit 36.

Disposed within the room 10 is a container of aqueous hydrogen peroxide solution 19 and associated air blower 21 which, during operation, blows vaporized hydrogen peroxide in controlled amounts into discharge wand 22A and 22B to mix with the output of ozone/oxygen therein. The amount of hydrogen peroxide being supplied is controlled by adjustment of the blower 21 through a connection thereof to the control panel 26. In an alternative arrangement, hydrogen peroxide can be supplied from generator 19 to the humidifier 14.

FIGS. 2A and 2B of the accompanying drawings show in more detail forms of dislodgement means 24A and 24B for use in the present invention, attached to the outlet, discharge ends of respective wands 22. The dislodgement means 24A has a jet outlet nozzle 38A at its extremity, and a generally circular plate 40 mounted on the wand 22A near the discharge end. The wand 22A passes through a central aperture 42 in a plate 40. The plate 40 has brush bristles 46A mounted on its lower surface, arranged in two arcs around the jet outlet nozzle 38A and protruding downwardly to an extent just beyond the extent of outlet from nozzle 38A. In use, oxygen/ozone gas mixture or oxygen/ozone/hydrogen peroxide gas mixture issues from nozzle 38A at relatively high pressure, and can be directed by the operator holding the wand to a carpet surface area while at the same time the operator scrubs the carpet surface area with the bristles 46A.

FIG. 2B shows an alternative but essentially similar arrangement, in which plate 40 is replaced by a wheeled platform 44 carrying two rotary brushes 46B and three gas jet outlets 38B for the oxygen/ozone/hydrogen peroxide delivery at pressure, located forwardly of the rotary brushes 46B.

FIG. 3 of the accompanying drawings illustrates the portability of a system according to the invention. Parts are numbered as in FIG. 1. A 4-wheeled cart 48 is provided, on which all the component parts of the system can be loaded for ease of transportation from one room to another. The instrumentation and control panel can be disconnected for transportation, and re-connected and disposed outside when the apparatus is placed in another room for use as shown in FIG. 1. The cart 48 is removed while the system is in use, but is loaded with the components after use, either for transportation to another room or for storage.

The operation of the system will be readily apparent from the preceding description of its component parts and their inter-connection. The cart 48 carrying the component parts is wheeled into the room 10 to be disinfected, and the parts are distributed around the room and connected together as illustrated in FIG. 1. An operator wearing a hazard suit and other appropriate protective clothing enters the room and holds the wand 22. The room is sealed. Conditions of treatment are set on the control panel 26, and the apparatus is switched on so that oxygen/ozone/hydrogen peroxide gas mixture at controlled ozone concentration, hydrogen peroxide concentration, relative humidity, temperature and elevated pressure issues from jet nozzle 38. The operator applies the jetted gas mixture to the carpet surfaces, drapery surfaces and other absorbent surfaces in the room, scrubbing the surfaces at the same time with the bristles 46. The room becomes pressurized above atmospheric pressure, due to the introduction of the oxygen/ozone gas mixture. Pressure is continually monitored by the control panel 26 to ensure safe working conditions for the operator, as well as the temperature, humidity and ozone concentration in the room. Smooth surfaces in the room may not need the action of the dislodgement means, but are satisfactorily disinfected by contact with the disinfecting atmosphere in the room. The oscillating fan 34 is operated throughout the procedure, to circulate the oxygen/ozone mixture throughout the room.

After a pre-set time of the procedure, and after all the appropriate, absorbent surfaces have been scrubbed, a time not normally exceeding 90 minutes, the hydrogen peroxide supply, the oxygen supply and ozone generator are switched off. Then the ozone destruct filter 36 is operated, sucking in the ozone-containing gases, destroying the ozone and issuing pure oxygen from it. The room can now be opened, the apparatus disconnected and loaded on the cart 48, and the room put back to its normal use.

Experimental Examples

Figure 4:
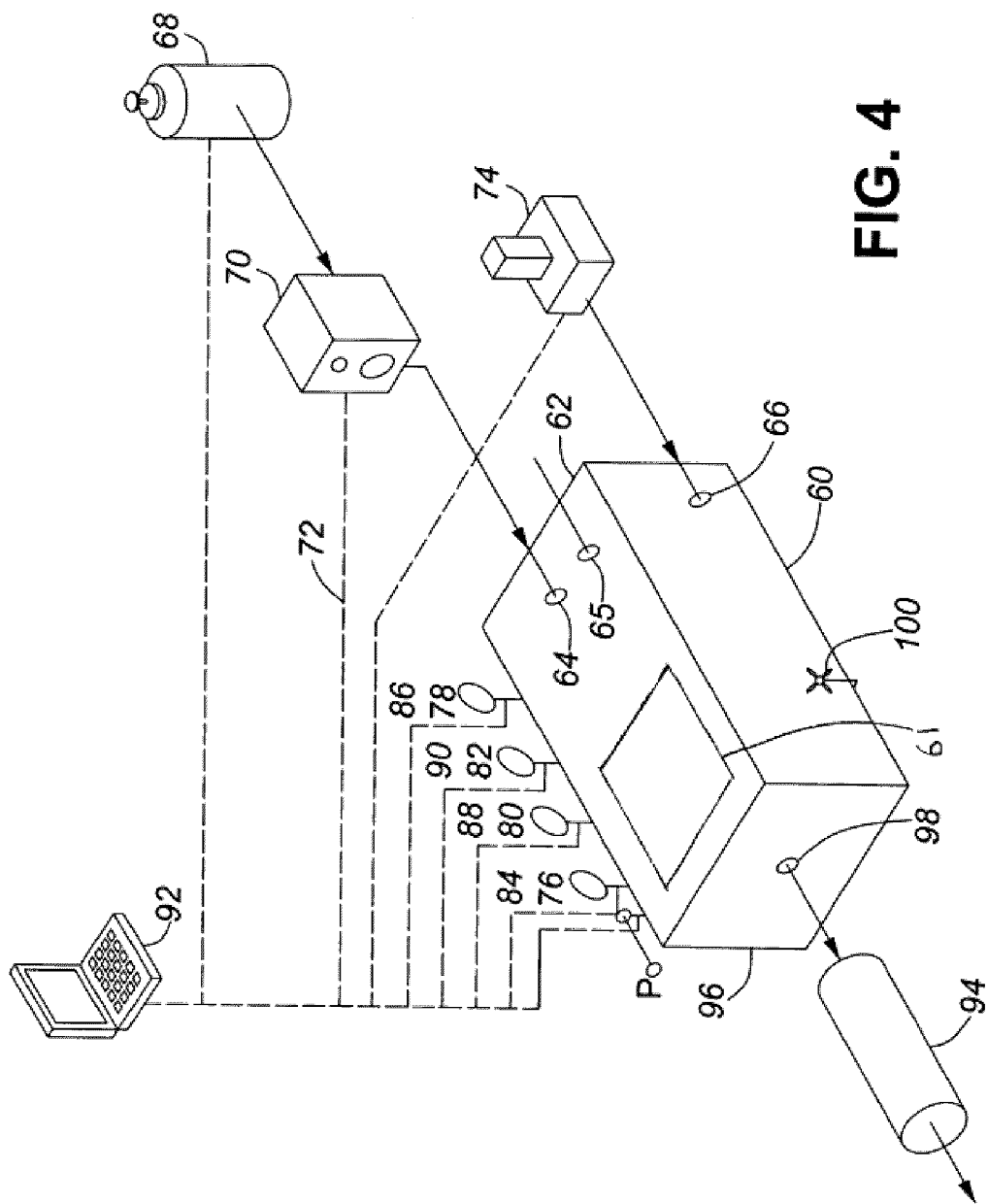
FIG. 4 is a diagrammatic illustration of a test apparatus used to generate some of the test results reported below.

Effective and optimum conditions for use in the present invention were determined using a laboratory apparatus as generally illustrated in FIG. 4 of the accompanying drawings.

A single pure colony of *Bacillus subtilis*, the surrogate for anthrax, was inoculated to a Columbia agar plate with 5% sheep's blood. They were incubated at 35° C. in room air for 18-24 hours. From the plate, 4-5 isolated colonies were selected, and suspended in tryptic soy broth to achieve a 0.5 McFarland turbidity standard ($1.5 \times 10^8$ cfu/ml) measured using a spectrophotometer. Inoculum was prepared by performing a series of serial dilutions of 0.9 ml 0.85 NaCl broth with 0.1 ml of original 0.5 McFarland inoculum ($6 \times 10$ fold) to give solutions of $10^{-1}$, $10^{-2}$, $10^{-3}$, $10^{-4}$, $10^{-5}$, $10^{-6}$ and $10^{-7}$ cfu/mL.

Organisms were plated out in triplicate, 0.1 ml of each solution being spread over the surface of Columbia sheep's blood agar plates. Two sets of 12 plates were subjected to ozone/oxygen exposure at preselected concentrations of ozone (ppm), humidity and temperature conditions in the illustrated apparatus. The other sets of 2 were treated as controls, with no ozone exposure, but kept at room temperature.

For ozone exposure, the apparatus generally illustrated in FIG. 4 was used.

The test plates were mounted inside a disinfection chamber 60, the upstream end 62 of which had an ozone inlet port 64, a hydrogen peroxide vapor inlet port 65 and a water vapor inlet port 66. A cylinder 68 of pressurized medical grade oxygen was provided, feeding oxygen to an ozone generator 70, equipped with alternating current electrical plates to which variable voltage could be supplied via input control 72. The output of oxygen/ozone mixed gas from the ozone generator 70 was fed to the ozone inlet port 64 of the disinfection chamber 60. A water vapor humidifier 74 supplied water vapor to inlet port 66. The disinfection chamber 60 also contained a heater/cooler (not shown), a temperature sensor 76, a pressure sensor 78, a humidity sensor 80 and an ozone sensor 82, connected electrically via respective lines 84, 86, 88 and 90 to a control panel and monitor 92, connected to feed back to the oxygen cylinder 68 to control flow for pressure adjustment purposes, to the ozone generator 70 to control and adjust the ozone quantity, to the water vapor humidifier 74 to control and adjust relative humidity in the disinfection chamber 60, and to the heater/cooler to control and adjust the temperature in the chamber. These parameters were all preset on the control panel to desired values and automatically re-adjusted themselves to these values as the experiments progressed.

An ozone destruct filter 94 was connected to the downstream end 96 of the disinfection chamber 60 at outlet port 98, to destroy ozone issuing from the chamber 60 at the end of the experiment. Gases were circulated within the chamber 60, and expelled therefrom at the termination of the experiment, using a fan 100 mounted therein. After placing the test plates in the chamber 60, it is sealed until the end of each experiment.

The control plates and the ozone treated plates were placed in an incubator at the same time. The plate counts were read through a microscope, and the numbers of colony forming units on each plate was counted. The spores are aerotolerant.

Example 1

Table 1 below provides a summary of experiments, whereby combinations of ozone, $H_2O_2$, humidity and exposure time were evaluated in terms of the ability to eliminate *Bacillus subtilis* when artificially applied as a biofilm onto non-porous surfaces such as stainless steel discs.

The steel discs for testing and the agar plates for testing were prepared, exposed and tested as described in the previous Example, with exposure conditions shown in Table 1 below. In some cases, indicated as "chamber", the tests were conducted with an apparatus generally as illustrated in FIG. 4. In other cases indicated as "room", the tests were conducted by exposing the disks and plates in a closed room, as generally illustrated in FIG. 1.

Table 1 also reports a period of post exposure (PEEP), in minutes, which is the time interval between the ozone/peroxide exposure termination and the start of the procedure for determining the results. This simulates real practice in disinfecting rooms where bacteria, after disinfectant treatment, die over a period of time. To allow for this, it is preferred that at least 25 minutes should elapse from the time the ozone/hydrogen peroxide exposure terminates before the disinfected room is put back into normal service.

TABLE 1

| *Bacillus Subtilus* *Bacillus subtilis* | | | | | | | |
|---|---|---|---|---|---|---|---|
| Material | O3 (PPM) | H2O2 % | Humidity % | Exp. | PEEP | Cham./Room | Log10 RED |
| Steel | 80 | 0.5 | 80-85 | 90 | 90 | Chamber | 0.5 |
| Steel | 80 | 1 | 80-85 | 90 | 0 | Chamber | 0.1 |
| Steel | 80 | 3 | 80-85 | 90 | 0 | Chamber | 7.23 |
| Steel | 0 | 3 | 80-85 | 90 | 90 | Chamber | 0 |
| Steel | 80 | 3 | 80-85 | 90 | 90 | Chamber | 7.23 |
| Steel | 80 | 1 | 80-85 | 90 | 90 | Chamber | 7.23 |
| Steel | 80 | 1 | 80-85 | 90 | 90 | Chamber | 4.61 |
| Steel | 80 | 1 | 80-85 | 90 | 90 | Chamber | 4.61 |
| Steel | 80 | 1 | 80-85 | 90 | 90 | Chamber | 4.61 |
| Steel | 80 | 1 | 80-85 | 90 | 90 | Room | 6.6 |
| Steel | 80 | 3 | 80-85 | 90 | 90 | Room | 6.6 |
| Steel | 80 | 3 | 80-85 | 90 | 0 | Room | 6.6 |
| Steel | 80 | 1 | 80-85 | 90 | 90 | Chamber | 6.34 |
| Steel | 80 | 3 | 80-85 | 90 | 90 | Chamber | 6.34 |
| Steel | 80 | 3 | 80-85 | 90 | 0 | Chamber | 6.34 |
| Carpet | 0 | 0 | 80-85 | 0 | 0 | Cham/Direct | 0 |
| Carpet | 80 | 1 | 80-85 | 90 | 0 | Cham/Direct | 1.13 |
| Carpet | 80 | 3 | 80-85 | 90 | 0 | Cham/Direct | 6.7 |
| Carpet | 80 | 3 | 80-85 | 90 | 0 | Cham/Indirect | 0.9 |

Example 2

Another series of experiments was conducted with the same *Bacillus subtilis* strain, but deposited onto fibrous carpet samples instead of steel discs. The carpet samples for testing and the agar plates for testing were prepared and tested as described for the steel discs above.

In the first run, a control, the *Bacillus*-carrying carpet sample was suspended in a room as depicted in FIG. 1, in an atmosphere containing no ozone and no hydrogen peroxide. After incubating a sample from the product and serial diluting as described, the viable colonies of *Bacillus* at 10-fold dilution were too numerous to count. At dilution $10^2$, a count of 227 was registered. At dilution $10^3$, the count was 15 and at dilution $10^4$ the count was 1.

In the second run, a *Bacillus*-carrying carpet sample was suspended as before but in an atmosphere containing 80 ppm ozone, 1% hydrogen peroxide and 80% relative humidity, the atmosphere being blown at the sample with a fan to cause physical agitation at its surface ("direct exposure"). The exposure time was 90 minutes. A zero count was achieved at all four serial dilutions.

In the third run, the a *Bacillus*-carrying carpet sample was suspended and agitated as in the second run ("direct exposure") but in an atmosphere containing 80 ppm ozone, 3% hydrogen peroxide and 80% relative humidity, exposure time 90 minutes. Again, zero counts were achieved at all four serial dilutions.

A fourth run repeated the third run as regards atmospheric composition in the room, but omitted the physical agitation of the surface indirect exposure"). The exposure time was 90 minutes. At dilution 10, a count of 218 was registered. At dilution $10^2$, a count of 21 was registered. At dilution $10^3$, the count was 8 and at dilution $10^4$ the count was 2.

Example 3

The third run of Example 2 was essentially repeated (Bacillus-carrying carpet, suspended in peroxide-ozone atmosphere in a room with fibrous surface agitation), using different hydrogen peroxide concentrations and exposure times, in an atmosphere containing 80 ppm ozone and humidity 80%.

The results are shown below in Table 2. Columns A, B, C and D are the counts of viable *Bacillus* colonies at the respective 10, 100, 1000 and 10000 dilutions. These results show optimum, complete destruction of *Bacillus* with 3% hydrogen peroxide and 60-90 minutes exposure, at 80 relative humidity and 80 ppm ozone.

TABLE 2

| Organism | Ozone (PPM) | H202 (%) | EXP (min) | Humidity | Discs/Carpet | A | B | C | D |
|---|---|---|---|---|---|---|---|---|---|
| Bacillus | 0 | 0% | 0 | 0 | Disc | TNTCT | NTC | 30 | 3 |
| Bacillus | 0 | 3% | 90 | 80 | Disc | TNTCT | NTC | 210 | 12 |
| Bacillus | 80 | 0% | 90 | 80 | Disc | TNTCT | NTC | 173 | 15 |
| Bacillus | 80 | 1% | 90 | 80 | Disc | 0 | 0 | 0 | 0 |
| Bacillus | 80 | 3% | 90 | 80 | Disc | 0 | 0 | 0 | 0 |
| Bacillus | 0 | 0% | 0 | 0 | Carpet | TNTC | 227 | 15 | 1 |
| Bacillus | 80 | 1% | 90 | 80 | Carpet/Direct | 0 | 0 | 0 | 0 |
| Bacillus | 80 | 3% | 90 | 80 | Carpet/Direct | 0 | 0 | 0 | 0 |
| Bacillus | 80 | 3% | 90 | 80 | Carpet/Indirect | 218 | 21 | 8 | 2 |
| Bacillus | 80 | 0% | 90 | 90 | Disc | TNTCT | NTC | 30 | 3 |
| Bacillus | 80 | 0% | 90 | 90 | Disc | TNTCT | NTC | 22 | 3 |
| Bacillus | 80 | 0% | 90 | 90 | Disc | TNTCT | NTC | 20 | 3 |
| Bacillus | 80 | 1% | 90 | 90 | Disc | 0 | 0 | 0 | 0 |
| Bacillus | 80 | 1% | 90 | 90 | Disc | 0 | 0 | 0 | 0 |
| Bacillus | 80 | 1% | 90 | 90 | Disc | 0 | 0 | 0 | 0 |
| Bacillus | 80 | 3% | 90 | 90 | Disc | 0 | 0 | 0 | 0 |
| Bacillus | 80 | 3% | 90 | 90 | Disc | 0 | 0 | 0 | 0 |
| Bacillus | 80 | 3% | 90 | 90 | Disc | 0 | 0 | 0 | 0 |
| Bacillus | 80 | 3% | 90 | 0 | Disc | 0 | 0 | 0 | 0 |
| Bacillus | 80 | 3% | 90 | 0 | Disc | 0 | 0 | 0 | 0 |
| Bacillus | 80 | 3% | 90 | 0 | Disc | 0 | 0 | 0 | 0 |

What is claimed is:

1. A process of combating anthrax and *C. botulinum* bacterium and spores thereof in an enclosed space, consisting of:
    exposing the bacterium and its spores in the enclosed space to a disinfecting atmosphere which includes ozone at an amount of 2-350 ppm by weight and hydrogen peroxide at an amount of 0.5-10 wt. %, at a relative humidity of at least 60%, wherein said amount of hydrogen peroxide is derived from a supply solution of 0.2%-10% hydrogen peroxide, and for a period of at least 30 minutes sufficient for an effective kill of the bacterium and spores; and
    subsequently removing ozone from the atmosphere, down to 0.04 ppm or less.

2. The process of claim 1 wherein the ozone amount in the disinfecting atmosphere is from 20-200 ppm by weight.

3. The process of claim 2 wherein the ozone concentration in the disinfecting atmosphere is from 35-100 ppm by weight.

4. The process of claim 1 wherein the hydrogen peroxide amount in the disinfecting atmosphere is from 1-5 wt. %.

5. The process of claim 1 wherein the period of exposure is from about 30 minutes to about 120 minutes.

6. The process of claim 1 wherein the period of exposure is from about 60 minutes to about 105 minutes.

7. The process of claim 1 wherein biofilm carrying surfaces are exposed to a localized stream of the disinfecting atmosphere.

8. The process of claim 7 wherein the pressure of the localized stream is from 14.7 to 100 psi.

9. A process of combating anthrax and *C. botulinum* bacterium and spores thereof in an enclosed space, consisting of:
    exposing the bacterium and its spores in the enclosed space to a disinfecting atmosphere which includes ozone at an amount of 2-350 ppm by weight and hydrogen peroxide at an amount of 0.5-10 wt. %, at a relative humidity of at least 60%, wherein said amount of hydrogen peroxide is derived from a supply solution of 0.2%-10% hydrogen peroxide, and for a period of at least 30 minutes sufficient for an effective kill of the bacterium and spores;

subjecting porous and fibrous surfaces within the room to physical agitation while exposed to the disinfecting atmosphere; and subsequently removing ozone from the atmosphere, down to 0.04 ppm or less.

10. The process of claim 9 wherein the ozone amount in the disinfecting atmosphere is from 20-200 ppm by weight.

11. The process of claim 10 wherein the ozone concentration in the disinfecting atmosphere is from 35-100 ppm by weight.

12. The process of claim 9 wherein the hydrogen peroxide amount in the disinfecting atmosphere is from 1-5 wt. %.

13. The process of claim 9 wherein the period of exposure is from about 30 minutes to about 120 minutes.

14. The process of claim 9 wherein the period of exposure is from about 60 minutes to about 105 minutes.

15. The process of claim 9 wherein the physical agitation is conducted with application of bristles.

16. The process of claim 9 wherein the physical agitation is conducted with application of air pressure jets.

17. The process of claim 9 wherein the physical agitation is conducted with application of ultrasonic energy, radio frequency energy, or electromagnetic waves, capable of causing physical disruption.

18. The process of claim 9 wherein the biofilm carrying surfaces are exposed to a localized stream of the disinfecting atmosphere.

19. The process of claim 18 wherein the pressure of the localized stream is from 14.7 to 100 psi.

* * * * *